" "

United States Patent
Gharpure et al.

(10) Patent No.: US 10,428,097 B2
(45) Date of Patent: Oct. 1, 2019

(54) PROCESS FOR PREPARATION OF FOSAPREPITANT DIMEGLUMINE AND AN INTERMEDIATE THEREOF

(71) Applicant: PIRAMAL ENTERPRISES LIMITED, Mumbai (IN)

(72) Inventors: Milind Gharpure, Mumbai (IN);
Prashant Ladkat, Mumbai (IN);
Navnath Shinde, Mumbai (IN);
Ashutosh Jagtap, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 15/779,910

(22) PCT Filed: Nov. 30, 2016

(86) PCT No.: PCT/IB2016/057194
§ 371 (c)(1),
(2) Date: May 30, 2018

(87) PCT Pub. No.: WO2017/093899
PCT Pub. Date: Jun. 8, 2017

(65) Prior Publication Data
US 2018/0354977 A1    Dec. 13, 2018

(30) Foreign Application Priority Data
Dec. 1, 2015 (IN) .......................... 4518/MUM/2015

(51) Int. Cl.
*C07F 9/6558*    (2006.01)

(52) U.S. Cl.
CPC ................................ *C07F 9/65583* (2013.01)

(58) Field of Classification Search
CPC .................................................. C07F 9/65583
See application file for complete search history.

(56) References Cited

U.S. PATENT DOCUMENTS

| 5,691,336 A | 11/1997 | Dorn et al. |
| 7,807,829 B2 | 10/2010 | McNamara et al. |
| 8,623,844 B2 | 1/2014 | Bhatt et al. |

FOREIGN PATENT DOCUMENTS

| IN | 2188/CHE/2011 | 3/2013 |
| IN | 1180/MUM/2013 | 4/2015 |
| WO | 2010/018595 A2 | 2/2010 |
| WO | 2013/168176 A2 | 11/2013 |

OTHER PUBLICATIONS

International Search Report (ISR) and Written Opinion (WO) dated Jan. 16, 2017 for International Application No. PCT/IB2016/057194.
Jeffrey J. Hale, et at.; Phosphorylated Morpholine Acetal Human Neurokinin-1 Receptor Antagonists as Water-Soluble Prodrugs; Journal of Medicinal Chemistry; 2000; vol. 43; pp. 1234-1241 by Merck Research Laboratories.

*Primary Examiner* — Rebecca L Anderson
(74) *Attorney, Agent, or Firm* — Ladas & Parry LLP

(57) ABSTRACT

The present invention relates to a novel process for the preparation of intermediate of fosaprepitant dimeglumine. The present invention particularly relates to a process for the preparation of fosaprepitant dibenzyl ester, an intermediate of fosaprepitant dimeglumine, which is simple, easy to handle on commercial scale and efficient.

4 Claims, No Drawings

PROCESS FOR PREPARATION OF FOSAPREPITANT DIMEGLUMINE AND AN INTERMEDIATE THEREOF

RELATED APPLICATION

This application is a national phase entry under 35 USC 371 of International Patent Application No.: PCT/IB2016/057194 filed on 30 Nov. 2016, which claims priority from Indian Application No. 4518/MUM/2015 filed on 1 Dec. 2015.

FIELD OF THE INVENTION

The present invention relates to a novel process for the preparation of an intermediate of fosaprepitant dimeglumine. More particularly, the present invention relates to a process for the preparation of fosaprepitant dibenzyl ester (represented herein by formula II), an intermediate of fosaprepitant dimeglumine. The present invention also relates to a process for the in-situ preparation of fosaprepitant dimeglumine, an antiemetic drug.

BACKGROUND OF THE INVENTION

Fosaprepitant, a prodrug of aprepitant is chemically known as [3-[[(2R,3S)-2-[(1R)-[3,5-bis(trifluoromethyl)phenyl]ethoxyl]-3-(4-fluorophenyl)-4-morpholinyl]methyl]-2,5-dihydro-5-oxo-1H-1,2,4-triazol-1-yl] phosphoric acid. The N-methyl-D-glucamine salt of fosaprepitant is approved for the treatment of emesis, nausea, cancer therapy toxicity and is available in the market as EMEND® in the US and as IVEMEND® in Europe. Fosaprepitant dimeglumine is structurally represented by following formula I,

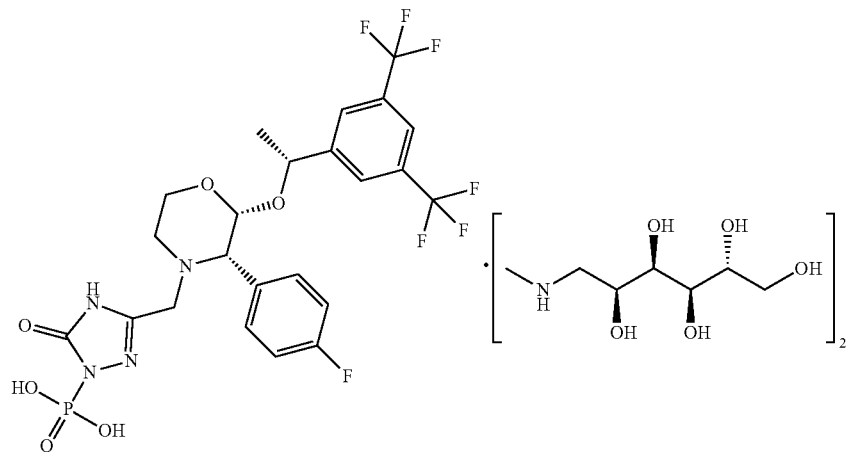

Formula I

Fosaprepitant, a phosphorylated aprepitant, when administered intravenously is rapidly converted to aprepitant, which is a substance P/neurokinin 1 (NK1) receptor antagonist. Emend® is used together with other medications to prevent nausea and vomiting that may be caused by surgery or cancer chemotherapy.

Fosaprepitant and its salts are disclosed in U.S. Pat. No. 5,691,336, which further discloses a process for manufacturing these compounds. The process for preparation of fosaprepitant dimeglumine disclosed in said patent involves two steps, which are schematically presented herein:

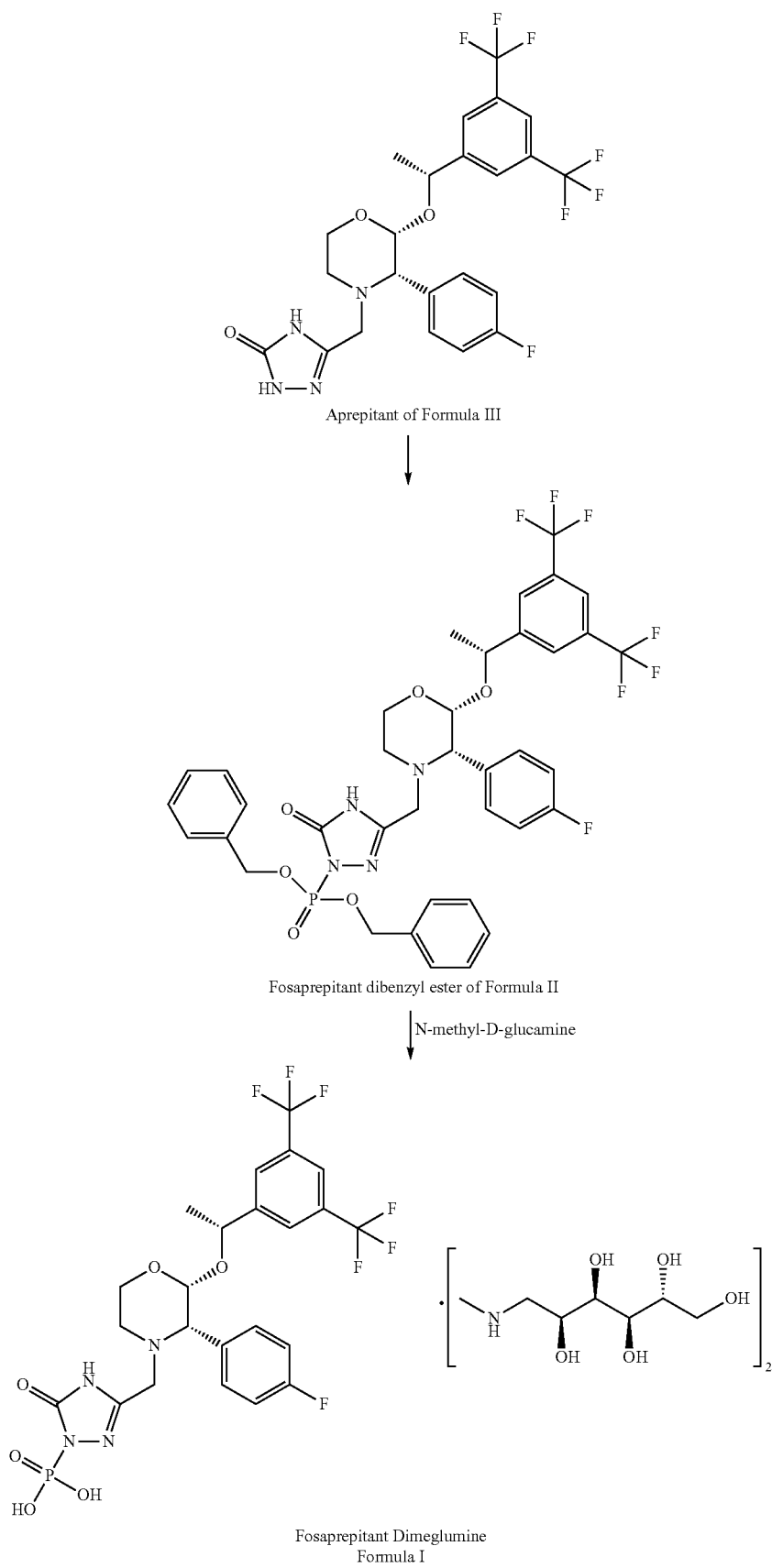

According to the US'336 Patent the process for preparation of fosaprepitant dimeglumine involves reaction of aprepitant with tetrabenzyl pyrophosphate using sodium bis(trimethylsilyl)amide (NaHMDS) as a base in the presence of THF as a solvent to obtain crude fosaprepitant dibenzyl ester. This crude fosaprepitant dibenzyl ester obtained is then treated with N-methyl-D-glucamine and Pd/C in the presence of methanol as a solvent to obtain fosaprepitant dimeglumine.

The article, *Journal of Medicinal Chemistry*, 2000, vol. 43, page no. 1234-1241 by Merck Research Laboratories describes in the preparation example of compound 4 that, the compound 4 is isolated as an oil after three chromatographic runs. However, the article does not disclose the purity of compound 4 achieved after three chromatographic runs.

U.S. Pat. No. 7,807,829 discloses monobenzyl fosaprepitant and its preparation method from aprepitant. The patent teaches that dibenzyl phosphoramidate compound (fosaprepitant dibenzyl ester) is very unstable and is present as an amorphous material, therefore the inventors of said patent converted unstable fosaprepitant dibenzyl ester to stable monobenzyl fosaprepitant.

U.S. Pat. No. 8,623,844 describes a process for preparation of isolated solid crystalline fosaprepitant dibenzyl ester from crude fosaprepitant dibenzyl ester. The process involves obtaining a solution of fosaprepitant dibenzyl ester in a solvent such as ethyl acetate, n-propyl acetate, isopropyl acetate, n-butyl acetate, isobutyl acetate, tertiary butyl acetate or mixture of solvents; followed by addition of an anti-solvent such as n-pentane, n-hexane, n-heptane, cyclohexane to recover fosaprepitant dibenzyl ester as a crystalline solid. The isolated solid crystalline fosaprepitant dibenzyl ester is of 93.74% purity and contains unknown impurities to an extent of 3.83%. The fosaprepitant dimeglumine prepared from said isolated solid crystalline fosaprepitant dibenzyl ester is of 94.5% purity and the purity of fosaprepitant dimeglumine after additional step of purification is enhanced to 99.76%.

Indian Patent Application No. 2188/CHE/2011 describes an improved process for preparation of fosaprepitant dimeglumine and its intermediate fosaprepitant dibenzyl ester. The process also teaches preparation of co-crystal of fosaprepitant dibenzyl ester with sodium chloride. However, the purity of fosaprepitant dibenzyl ester prepared using said process is not reported in the IN'2188 application. Further, the fosaprepitant dimeglumine prepared using said improved process has purity of at least about 97.1%, which is not a pharmaceutically acceptable grade purity of fosaprepitant dimeglumine. Moreover, the improved process disclosed in IN'2188 application is very lengthy, tedious and involves use of thiophenol resin in the preparation process, which may result in the presence of sulfur content in the fosaprepitant dimeglumine.

The API, fosaprepitant dimeglumine is a highly sensitive moiety and multiple purifications to achieve pharmaceutically acceptable grade purity leads to degradation of fosaprepitant dimeglumine to aprepitant. Therefore, there is a need to prepare highly pure fosaprepitant dibenzyl ester and then convert it to fosaprepitant dimeglumine in order to achieve pharmaceutically acceptable grade purity.

The afore discussed prior art references provide processes for the preparation of fosaprepitant dibenzyl ester and its conversion to fosaprepitant dimeglumine involves either chromatographic purification of fosaprepitant dibenzyl ester oil or isolation of solid crystalline fosaprepitant dibenzyl ester. However in case of column chromatographic purification of fosaprepitant dibenzyl ester oil, the purification involves three chromatographic runs, which is tedious, lengthy and commercially non-feasible process. Further, the non-disclosure of purity of fosaprepitant dibenzyl ester after three chromatographic runs leads to an uncertainty.

Although, U.S. Pat. No. 8,623,844 teaches isolation of solid crystalline fosaprepitant dibenzyl ester, the isolated fosaprepitant dibenzyl ester is unstable and highly hygroscopic in nature and even slight exposure to air will degrade fosaprepitant dibenzyl ester to fosaprepitant monobenzyl ester and/or aprepitant, therefore the fosaprepitant dibenzyl ester obtained according to US'844 patent cannot be stored. Thus, the said process is commercially non-viable. Further, the purity of fosaprepitant dibenzyl ester and its converted fosaprepitant dimeglumine, without additional step of purification is 94.5%, which is not of pharmaceutically acceptable grade.

Thus, there is a need to develop a robust process for preparation of highly unstable fosaprepitant dibenzyl ester and its conversion to fosaprepitant dimeglumine, which is industrially acceptable, commercially viable and provides purity of pharmaceutically acceptable grade, without any additional step of purification.

OBJECTS OF THE INVENTION

An object of the present invention is to provide a process for preparation of pure fosaprepitant dibenzyl ester of formula II.

Another object of the present invention is to provide a process for the preparation of fosaprepitant dibenzyl ester, wherein the purity of fosaprepitant dibenzyl ester is >96%.

An object of the present invention is to provide a process for the in-situ preparation of fosaprepitant dimeglumine of formula I from aprepitant of formula III.

Yet another object of the present invention is to provide a process for the preparation of fosaprepitant dimeglumine from said pure fosaprepitant dibenzyl ester, wherein the purity of fosaprepitant dimeglumine is >99%, without any additional step of purification.

SUMMARY OF THE INVENTION

In accordance with an aspect of the present invention, there is provided a process for the preparation of intermediate of fosaprepitant dimeglumine. The present invention particularly provides a process for the preparation of [3-[[(2R,3S)-2-[(1R)-1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl]-phosphonic acid bis(phenylmethyl) ester (fosaprepitant dibenzyl ester) of formula II, Formula II

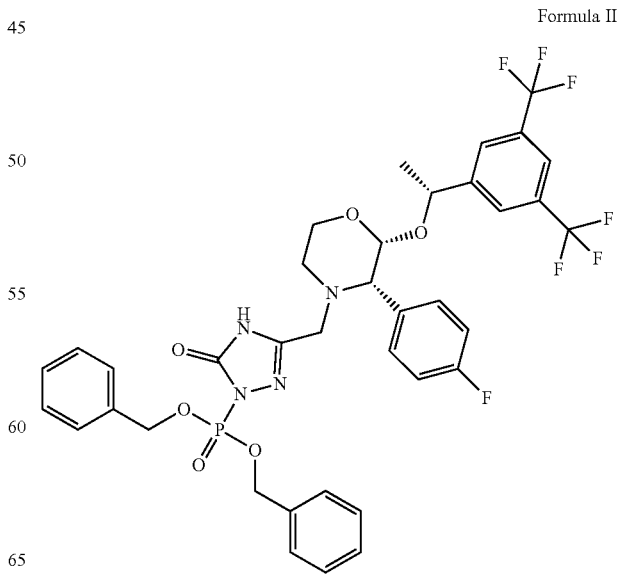

comprising the steps of,
(a) obtaining a solution of fosaprepitant dibenzyl ester of formula II in at least one solvent or a mixture of solvents thereof,
(b) adding an inorganic acid to the solution obtained in step (a),
(c) concentrating the reaction mass obtained in step (b),
(d) adding at least one solvent or a mixture of solvents thereof to the reaction mass obtained in step (c),
(e) filtering the reaction mass obtained in step (d) to obtain a residue, Residue-A,
(f) adding at least one solvent or a mixture of solvents thereof to the residue obtained in step (e),
(g) filtering the reaction mass obtained in step (f) to obtain a residue, Residue-B,
(h) adding at least one solvent or a mixture of solvents thereof to the residue obtained in step (g),
(i) filtering the reaction mass obtained in step (h),
(j) concentrating the filtrate obtained in step (i) to yield fosaprepitant dibenzyl ester of purity >96%.

In accordance with another aspect of the present invention, there is provided a process for the in-situ preparation of 1-deoxy-1-(methylamino)-D-Glucitol[3-[[(2R,3S)-2-[(1R)-1-[3,5-bis(trifluoromethyl) phenyl] ethoxyl]-3-(4-fluorophenyl)-4-morpholinyl]methyl]-2,5-dihydro-5-oxo-1H-1,2,4-triazol-1-yl] phosphonate (2:1) salt (fosaprepitant dimeglumine) of formula I, (ix) adding at least one solvent or a mixture of solvents thereof to the residue obtained in step (viii),
(x) filtering the reaction mass obtained in step (ix) and concentrating the filtrate to yield fosaprepitant dibenzyl ester of purity >96% as an oil,
(xi) dissolving the oil obtained in step (x) in at least one solvent or a mixture of solvents thereof,
(xii) adding N-methyl-D-glucamine and Pd/C to the reaction mass obtained in step (xi) and hydrogenating the reaction mass for 8 h to 14 h at 2 kg to 8 kg pressure,
(xiii) filtering the reaction mass obtained in step (xii),
(xiv) adding metal scavenger to the reaction mass obtained in step and stirring for 14 h,
(xv) obtaining fosaprepitant dimeglumine of purity 99% from the resulting reaction mass of step (xiv) on further work-up.

In accordance with another aspect of the present invention, the process of the present invention overcomes the disadvantages associated with the processes described in the prior art, which involves use of multiple column chromatography for purification of fosaprepitant dibenzyl ester or involves the isolation of unstable crystalline fosaprepitant dibenzyl ester.

Formula I

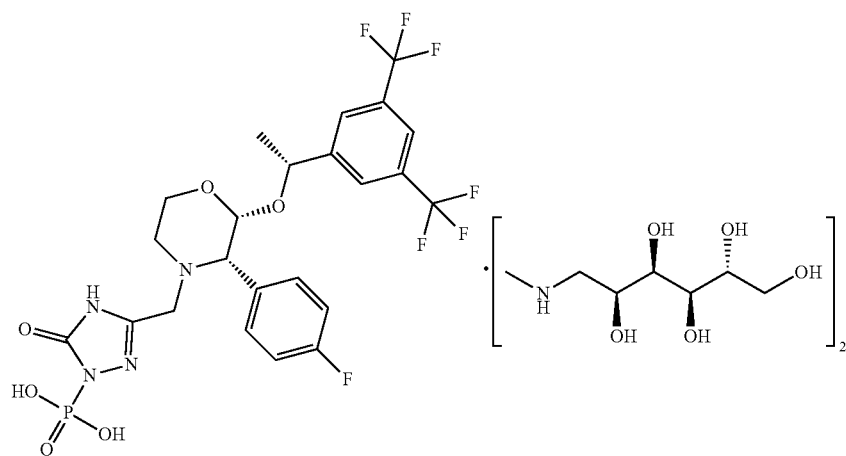

comprising the steps of,
(i) treating aprepitant of formula III with tetrabenzyl pyrophosphate using a base in the presence of a solvent at a temperature of −35° C. to 0° C. for 1 h to 4 h to obtain fosaprepitant dibenzyl ester,
(ii) adding at least one solvent or a mixture of solvents to the reaction mass obtained in step (i),
(iii) adding an inorganic acid to the reaction mass obtained in step (ii),
(iv) concentrating the reaction mass obtained in step (iii),
(v) adding at least one solvent or a mixture of solvents thereof to the reaction mass obtained in step (iv),
(vi) filtering the reaction mass obtained in step (v) to obtain a residue, Residue-A,
(vii) adding at least one solvent or a mixture of solvents thereof to the residue obtained in step (vi),
(viii) filtering the reaction mass obtained in step (vii) to obtain a residue, Residue-B, The inventors of the present invention surprisingly found that use of an inorganic acid in the process results in highly pure fosaprepitant dibenzyl ester. The inorganic acid used in the process is simple, easy to handle on commercial scale and cost-effective; thereby making the process for preparation of fosaprepitant dibenzyl ester and its conversion to fosaprepitant dimeglumine simple, efficient and industrially applicable.

DETAILED DESCRIPTION OF THE INVENTION

The present invention relates to a process for the preparation of [3-[[(2R,3S)-2-[(1R)-[3,5-bis(trifluoromethyl)phenyl]ethoxyl]-3-(4-fluorophenyl)-4-morpholinyl]methyl]-2,5-dihydro-5-oxo-1H-1,2,4-triazol-1-yl]phosphonic acid bis(phenylmethyl) ester (fosaprepitant dibenzyl ester) of formula II, Formula II

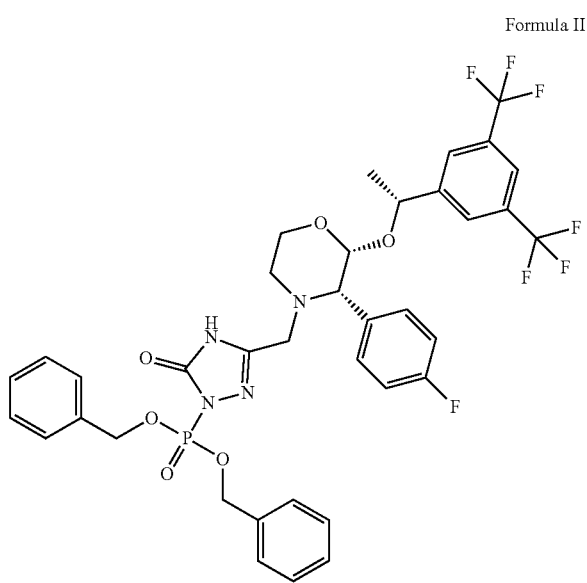 [SMILES: C[C@@H](O[C@H]1OCCN(Cc2nn(P(=O)(OCc3ccccc3)OCc3ccccc3)c(=O)[nH]2)[C@H]1c1ccc(F)cc1)c1cc(C(F)(F)F)cc(C(F)(F)F)c1]

comprising the steps of,
(a) obtaining a solution of fosaprepitant dibenzyl ester of formula II in at least one solvent or a mixture of solvents thereof,
(b) adding an inorganic acid to the solution obtained in step (a),
(c) concentrating the reaction mass obtained in step (b),
(d) adding at least one solvent or a mixture of solvents thereof of the reaction mass obtained in step (c),
(e) filtering the reaction mass obtained in step (d) to obtain a residue, Residue-A,
(f) adding at least one solvent or a mixture of solvents thereof to the residue obtained in step (e),
(g) filtering the reaction mass obtained in step (f) to obtain a residue, Residue-B,
(h) adding at least one solvent or a mixture of solvents thereof to the residue obtained in step (g),
(i) filtering the reaction mass obtained in step (h),
(j) concentrating the filtrate obtained in step (i) to yield fosaprepitant dibenzyl ester of purity >96%.

The term, 'pharmaceutically acceptable grade' used herein refers to the Fosaprepitant Dimeglumine of formula I of purity ≥99%, fosaprepitant dimeglumine is not listed in any pharmacopeia.

In an embodiment of the present invention, in the step (a) of the process a solution of fosaprepitant dibenzyl ester is prepared by dissolving fosaprepitant dibenzyl ester in at least one solvent or a mixture of solvents. The fosaprepitant dibenzyl ester used at this step can be obtained from reaction of aprepitant with tetrabenzyl pyrophosphate in the presence of a base and a solvent, as described in the U.S. Pat. No. 5,691,336. Also, the fosaprepitant dibenzyl ester prepared by any process can be used in-side at this step of the process.

The fosaprepitant dibenzyl ester used in step (a) of the process obtained according to the process described in U.S. Pat. No. 5,691,336 or prepared by any other process known in the prior art is of purity <78%.

The solvent(s) used for preparing the fosaprepitant dibenzyl ester solution in step (a) of the process is selected from the group consisting of a polar solvent and a non-polar solvent or a mixture thereof.

The solvent(s) used in the step (a) of the process is selected from, but not limited to methyl tert-butyl ether, tetrahydrofuran, toluene, acetone, isobutyl methyl ketone, ethyl acetate, dichloromethane and cyclohexane a mixture thereof.

The solution of fosaprepitant dibenzyl ester of step (a) can be prepared by addition of one solvent or by addition of more than one solvents, that is two, three or more solvents sequentially, or as a mixture of solvents.

In an embodiment of the present invention, in the step (b) of the process an inorganic acid is added to the solution of fosaprepitant dibenzyl ester obtained in step (a). The said inorganic acid is selected from, but not limited to boric acid.

In accordance with embodiment of said process step (b), the inorganic acid charged is about 0.5 to 5 equivalents based on the quantity of fosaprepitant dibenzyl ester of formula II.

In an embodiment of the present invention, in the step (c) of the process the reaction mass obtained after treatment with inorganic acid in the step (b) is concentrated or evaporated to dryness. The concentration of reaction mass is carried out at a temperature lower than 40° C. The reaction mass obtained after concentration is light yellow to brown thick sticky mass.

In an embodiment of the present invention, in the step (d) of the process the reaction mass obtained after concentration in step (c) is charged with at least one solvent or a mixture of solvents. The said solvent(s) is selected from the group consisting of a polar solvent and a non-polar solvent or a mixture thereof.

The solvent(s) used in the step (d) of the process is selected from, but not limited to methyl tert-butyl ether, tetrahydrofuran, toluene, acetone, isobutyl methyl ketone, ethyl acetate, dichloromethane and cyclohexane or a mixture thereof.

In an embodiment, a single solvent is added to the reaction mass of step (c). In another embodiment, the addition of more than one solvent, that is two, three or more solvents to the reaction mass of step (c) can be made sequentially or can be added as a mixture of solvents.

The ratio of at least one solvent or mixture of solvents used in step (d) above to the solution in step (c) is about 2 volume to 20 volume. The ratio of solvents when more than one solvent is used in step (d) is about 1 volume to 16 volume.

In the step (d) of the process reaction mass obtained after the addition of at least one solvent or a mixture of solvents is stirred at a temperature lower than 50° C. for 0.5 h to 5 h.

In an embodiment of the present invention, in the step (e) of the process the reaction mass obtained in the step (d) after addition of at least one solvent or a mixture of solvents thereof is filtered to obtain a residue. For the purpose of clarity the residue obtained in step (e) is referred to as 'Residue-A'.

In an embodiment of the present invention, in the step (f) of the process the residue obtained in step (e) after filtration is charged with at least one solvent or a mixture of solvents. The said solvent(s) is selected from the group consisting of a polar solvent and a non-polar solvent or a mixture thereof.

The solvent(s) used in the step (f) of the process is selected from, but not limited to methyl tert-butyl ether, tetrahydrofuran, toluene, acetone, isobutyl methyl ketone, ethyl acetate, dichloromethane and cyclohexane or a mixture thereof.

In an embodiment, a single solvent is added to the residue obtained in step (e). In another embodiment, the addition of more than one solvent, that is two, three or more solvents to the residue obtained in step (e) can be made sequentially or can be added as a mixture of solvents.

The ratio of at least one solvent or mixture of solvents used in step (f) above to the residue in step (e) is about 2 volume to 20 volume. The ratio of solvents when more than one solvent is used in step (f) is about 1 volume to 16 volume.

In the step (f) the reaction mass obtained after the addition of at least one solvent or a mixture of solvents is stirred at a temperature lower than 50° C. for 0.5 h to 5 h.

using sodium sulphate and concentrated at a temperature lower than 40° C. to yield thick oily syrup of fosaprepitant dibenzyl ester of purity >96%.

The present invention also relates to a process for the in-situ preparation of 1-deoxy-1-(methylamino)-D-Glucitol [3-[[(2R,3S)-2-[(1R)-1-[3,5-bis(trifluoromethyl) phenyl] ethoxy]-3-(4-fluorophenyl)-4-morpholinyl]methyl]-2,5-dihydro-5-oxo-1H-1,2,4-triazol-1-yl] phosphonate (2:1) salt (fosaprepitant dimeglumine) of formula I,

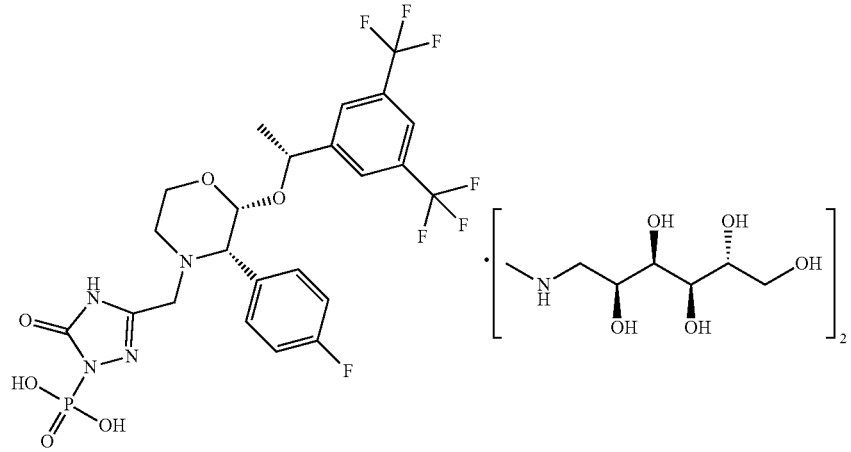

Formula I

In an embodiment of the present invention, in the step (g) of the process the reaction mass obtained in the step (f) after addition of at least one solvent or a mixture of solvents thereof is filtered to obtain a residue. For the purpose of clarity the residue obtained in step (g) is referred to as 'Residue-B'.

In an embodiment of the present invention, in the step (h) of the process, the residue obtained in step (g) after filtration is charged with at least one solvent or a mixture of solvents. The said solvent(s) is selected from the group consisting of a polar solvent and a non-polar solvent or a mixture thereof.

The solvent(s) used in the step (h) of the process is selected from, but not limited to methyl tert-butyl ether, tetrahydrofuran, toluene, acetone, isobutyl methyl ketone, ethyl acetate, dichloromethane and cyclohexane or a mixture thereof.

In an embodiment, a single solvent is added to the residue obtained step (g). In another embodiment, the addition of more than one solvent, that is two, three or more solvents to the residue obtained in step (g) can be made sequentially or can be added as a mixture of solvents.

The ratio of at least one solvent or mixture of solvents used in step (h) above to the residue in step (g) is about 2 volume to 12 volume. The ratio of solvents when more than one solvent is used in step (f) is about 1 volume to 16 volume.

In the step (h), the reaction mass obtained after the addition of at least one solvent or a mixture of solvents is stirred at a temperature lower than 40° C. for 0.5 h to 5 h.

In an embodiment of the present invention, in the step (i) of the process the reaction mass obtained in the step (h) after addition of at least one solvent or a mixture of solvents thereof is filtered and the filtrate is washed with solution of sodium chloride. The resulting filtrate organic layer is dried comprising the steps of,
(i) treating aprepitant of formula III with tetrabenzyl pyrophosphate using a base in the presence of a solvent at a temperature of −35° C. to 0° C. for 1 h to 4 h to obtain fosaprepitant dibenzyl ester,
(ii) adding at least one solvent or a mixture of solvents to the reaction mass obtained in step (i),
(iii) adding an inorganic acid to the reaction mass obtained in step (ii),
(iv) concentrating the reaction mass obtained in step (iii),
(v) adding at least one solvent or a mixture of solvents thereof to the reaction mass obtained in step (iv),
(vi) filtering the reaction mass obtained in step (v) to obtain a residue, Residue-A,
(vii) adding at least one solvent or a mixture of solvents thereof to the residue obtained in step (vi),
(viii) filtering the reaction mass obtained in step (vii) to obtain a residue, Residue-B,
(ix) adding at least one solvent or a mixture of solvents thereof to the residue obtained in step (viii),
(x) filtering the reaction mass obtained in step (ix) and concentrating the filtrate to yield fosaprepitant dibenzyl ester of purity >96% as an oil,
(xi) dissolving the oil obtained in step (x) in at least one solvent or a mixture of solvents thereof,
(xii) adding N-methyl-D-glucamine and Pd/C to the reaction mass obtained in step (xi) and hydrogenating the reaction mass for 8 h to 14 h at 2 kg to 8 kg pressure,
(xiii) filtering the reaction mass obtained in step (xii),
(xiv) adding metal scavenger to the reaction mass obtained in step and stirring for 8 h to 14 h,
(xv) obtaining fosaprepitant dimeglumine of purity 99% from the resulting reaction mass of step (xiv) on further work-up.

The compound of formula III, aprepitant is a known compound and can be prepared by a person skilled in the art by following the processes known in the art. For example the U.S. Pat. No. 5,719,147 discloses aprepitant of formula II and its preparation method.

In an embodiment of the present invention, in the step (ii) of the process a solution of fosaprepitant dibenzyl ester is prepared by dissolving fosaprepitant dibenzyl ester in at least one solvent or a mixture of solvents. The fosaprepitant dibenzyl ester used at this step can be obtained from reaction of aprepitant with tetrabenzyl pyrophosphate in the presence of a base and a solvent, as described in the U.S. Pat. No. 5,691,336. Also, the fosaprepitant dibenzyl ester prepared by any process can be used in-situ at this step of the process.

The fosaprepitant dibenzyl ester used in step (ii) of the process obtained according to the process described in U.S. Pat. No. 5,691,336 or prepared by any other process known in the prior art is of purity <78%.

The solvent(s) used for preparing the fosaprepitant dibenzyl ester solution in step (ii) of the process is selected from the group consisting of a polar solvent and a non-polar solvent or a mixture thereof.

The solvent(s) used in the step (ii) of the process is selected from, but not limited to methyl tert-butyl ether, tetrahydrofuran, toluene, acetone, isobutyl methyl ketone, ethyl acetate, dichloromethane and cyclohexane or a mixture thereof.

The solution of fosaprepitant dibenzyl ester of step (ii) can be prepared by addition of one solvent or by addition of more than one solvent, that is two, three or more solvents sequentially, or as a mixture of solvents.

In an embodiment of the present invention, in the step (iii) of the process an inorganic acid is added to the solution of fosaprepitant dibenzyl ester obtained in step (ii). The said inorganic acid is selected from, but not limited to boric acid.

In accordance with embodiment of said process step (iii), the inorganic acid charged is about 0.5 to 5 equivalents based on the quantity of fosaprepitant dibenzyl ester of formula II.

In an embodiment of the present invention, in the step (iv) of the process the reaction mass obtained after treatment with inorganic acid in the step (iii) is concentrated or evaporated to dryness. The concentration of reaction mass is carried out at a temperature lower than 40° C. The reaction mass obtained after concentration is light yellow to brown thick sticky mass.

In an embodiment of the present invention, in the step (v) of the process the reaction mass obtained after concentration in step (iv) is charged with at least one solvent or a mixture of solvents. The said solvent(s) is selected from the group consisting of a polar solvent and a non-polar solvent or a mixture thereof.

The solvent(s) used in the step (d) of the process is selected from, but not limited to methyl tert-butyl ether, tetrahydrofuran, toluene, acetone, isobutyl methyl ketone, ethyl acetate, dichloromethane and cyclohexane or a mixture thereof.

In an embodiment, a single solvent is added to the reaction mass of step (iv). In another embodiment, the addition of more than one solvent, that is two, three or more solvents to the reaction mass of step (iv) can be made sequentially or can be added as a mixture of solvents.

The ratio of at least one solvent or mixture of solvents used in step (v) above to the solution in step (iv) is about 2 volume to 20 volume. The ratio of solvents when more than one solvent is used in step (v) is about 1 volume to 16 volume.

In the step (v) of the process reaction mass obtained after the addition of at least one solvent or a mixture of solvents is stirred at a temperature lower than 50° C. for 0.5 h to 5 h.

In an embodiment of the present invention, in the step (vi) of the process the reaction mass obtained in the step (v) after addition of at least one solvent or a mixture of solvents thereof is filtered to obtain a residue. For the purpose of clarity the residue obtained in step (vi) is referred to as 'Residue-A'.

In an embodiment of the present invention, in the step (vii) the process the residue obtained in step (vi) after filtration is charged with at least one solvent or a mixture of solvents. The said solvent(s) is selected from the group consisting of a polar solvent and a non-polar solvent or a mixture thereof.

The solvent used in the step (vii) of the process is selected from, but not limited to methyl tert-butyl ether, tetrahydrofuran, toluene, acetone, isobutyl methyl ketone, ethyl acetate, dichloromethane and cyclohexane or a mixture thereof.

In embodiment, a single solvent is added to the residue obtained in step (vi). In another embodiment, the addition of more than one solvent, that is two, three or more solvents to the residue obtained in step (vi) can be made sequentially or can be added as a mixture of solvents.

The ratio of at least one solvent or mixture of solvents used in step (vii) above to the residue in step (vi) is about 2 volume to 20 volume. The ratio of solvents when more than one solvent is used in step (vii) is about 1 volume to 16 volume.

In the step (vii) the reaction mass obtained after the addition of at least one solvent or a mixture of solvents is stirred at a temperature lower than 50° C. for 0.5 h to 5 h.

In an embodiment of the present invention, in the step (viii) of the process the reaction mass obtained in the step (vii) after addition of at least one solvent or a mixture of solvents thereof is filtered to obtain a residue. For the purpose of clarity the residue obtained in step (g) is referred to as 'Residue-B'.

In an embodiment of the present invention, in the step (ix) of the process, the residue obtained in step (viii) after filtration is charged with at least one solvent or a mixture of solvents. The said solvent(s) is selected from the group consisting of a polar solvent and a non-polar solvent or a mixture thereof.

The solvent(s) used in the step (ix) of the process is selected from, but not limited to methyl tert-butyl ether, tetrahydrofuran, toluene, acetone, isobutyl methyl ketone, ethyl acetate, dichloromethane and cyclohexane or a mixture thereof.

In an embodiment, a single solvent is added to the residue obtained in step (viii). In another embodiment, the addition of more than one solvent, that is two, three or mare solvents to the residue obtained in step (viii) can be made sequentially or can be added as a mixture of solvents.

The ratio of at least one solvent or mixture of solvents used in stop (ix) above to the residue in step (viii) is about 2 volume to 12 volume. The ratio of solvents when more than one solvent is used in step (vii) is about 1 volume to 16 volume.

In the step (ix), the reaction mass obtained after the addition of at least one solvent or a mixture of solvents is stirred at a temperature lower than 40° C. for 0.5 h to 5 h.

In an embodiment of the present invention, in the step (x) of the process of the reaction mass obtained in the step (ix) after addition of at least one solvent or a mixture of solvents thereof is filtered. The resulting filtrate organic layer is dried using sodium sulphate and concentrated at a temperature lower 40° C. to yield thick oily syrup of fosaprepitant dibenzyl ester of purity >96%.

In an embodiment of the present invention, in the step (xiv), the metal scavenger of the process added to the reaction mass obtained in the step (xiii) can be selected from but not limited to triphenyl phosphine and tributyl phosphine.

The following examples which fully illustrate the practice of the preferred embodiments of the present invention are intended to be for illustrative purpose only and should not be considered in anyway to limit the scope of the present invention.

EXAMPLES

Example-1: Preparation of Fosaprepitant Dibenzyl Ester

To a reaction flask was charged fosaprepitant dibenzyl ester of formula II (170 g) and methyl tert-butyl ether (1000 mL) to obtain a solution. Then boric acid (100 g) was added to the resulting solution and the obtained reaction mass was concentrated at a temperature of 30° C. to obtain a light yellow to brown thick sticky mass. To this sticky mass, toluene (300 mL) was charged followed by cyclohexane (2000 mL) and the reaction mass was stirred at a temperature of 30° C. for 1 h to 2 h. The resulting reaction mass was then filtered, washed with 13% solution of toluene in cyclohexane to obtain Residue-A. To the obtained Residue-A acetone (300 mL) was charged followed by cyclohexane (2000 mL) and the reaction mass was stirred at a temperature of 30° C. for 1 h to 2 h. The resulting reaction mass was then filtered and washed with 13% solution of acetone in cyclohexane to obtain Residue-B. To the Residue-B obtained, was charged ethyl acetate (500 mL), and the reaction mass was stirred and filtered. The filtrate was then washed twice with 10% solution of sodium chloride (500 mL). The resulting organic layer of ethyl acetate was dried over anhydrous sodium sulphate. The ethyl acetate layer was then concentrated under vacuum at a temperature of 30° C. to yield fosaprepitant dibenzyl ester of formula II as an oil of 99.18% purity and a yield of 74%.

Example-2: Preparation of Fosaprepitant Dimeglumine

To fosaprepitant dibenzyl ester (110 g) of formula II as an oil obtained in example-1, methanol (800 mL) added and stirred for a while followed by addition of 5% Pd/C and methanol (110 mL). Hydrogen pressure 2.5 kg/cm² to 3.0 kg/cm² was applied and stirred at 20-30° C. for 4 h. N-methyl D-glutamine (55 g) and methanol (200 mL) was added into the reaction mixture and hydrogen pressure 2.5 kg/cm² to 3.0 kg/cm² was applied. The reaction mixture was stirred at 20-30° C. for 20 h. Pd/C was filtered from the reaction mixture and fresh methanol (220 mL) was added into it followed by addition of tributyl phosphine (6.6 mL), methanol (220 mL) and stirred for about 20-23 h under nitrogen at 20-30° C. To the reaction mixture activated carbon (11 g) was added and stirred for about 1 h. The reaction mixture was filtered and concentrated under vacuum up to ~2.0-3.5 volume at 20-30° C. Then after 11% orthophosphoric acid solution was added to adjust the pH reaction mass to 7.5-8.5 followed by addition of methanol (300 mL) and isopropyl alcohol (2750 mL) to the reaction mixture. The reaction mixture was stirred for 1 h, filtered and washed with mixture of methanol and isopropyl alcohol solution, acetone and methyl tert-butyl ether followed by drying at under vacuum below 25° C. for 3-4 h to yield fosaprepitant dimeglumine (50-64%) having purity more than 99%.

We claim:
1. A process for the in-situ preparation of 1-deoxy-1-(methylamino)-D-Glucitol[3-[[(2R,3S)-2-[(1R)-1-[3,5-bis (trifluoromethyl) phenyl] ethoxy]-3-(4-fluorophenyl)-4-morpholinyl]methyl]-2,5-dihydro-5-oxo-1H-1,2,4-triazol-1-yl] phosphonate (2:1) salt (fosaprepitant dimeglumine) of formula I,

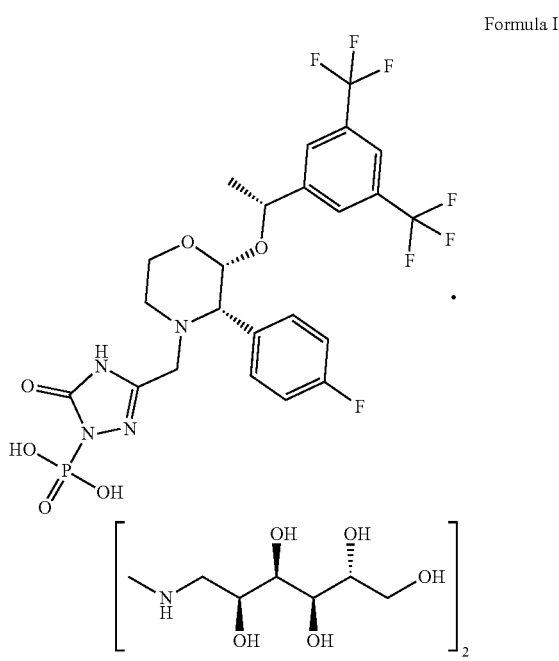

Formula I comprising the steps of,
(i) treating aprepitant of formula III,

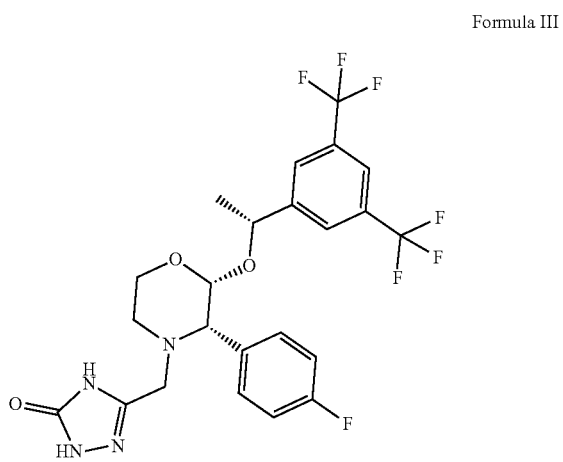 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

Formula III with tetrabenzyl pyrophosphate using a base in the presence of a solvent at a temperature of −35° C. to 0° C. for 1 h to 4 h to obtain fosaprepitant dibenzyl ester of formula II, Formula II

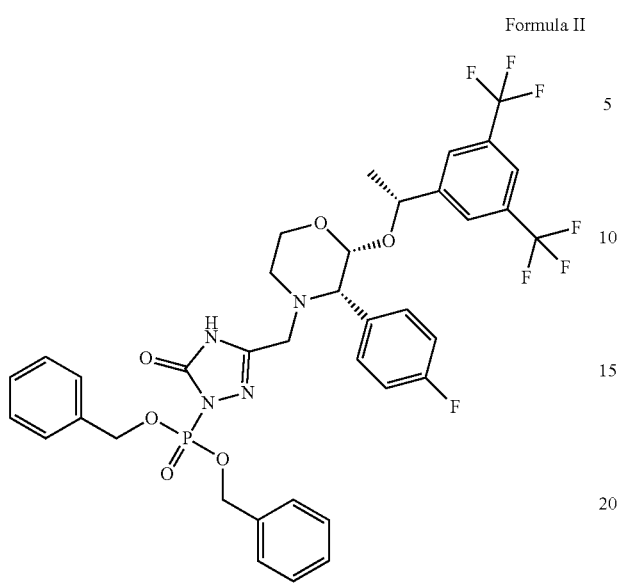

(ii) adding at least one solvent or a mixture of solvents to the reaction mass obtained in step (i),
(iii) adding an inorganic acid to the reaction mass obtained in step (ii),
(iv) concentrating the reaction mass obtained in step (iii),
(v) adding at least one solvent or a mixture of solvents thereof to the reaction mass obtained in step (iv),
(vi) filtering the reaction mass obtained in step (v) to obtain a residue, Residue-A,
(vii) adding at least one solvent or a mixture of solvents thereof to the residue obtained in step (vi),
(viii) filtering the reaction mass obtained in step (vii) to obtain a residue, Residue-B,
(ix) adding at least one solvent or a mixture of solvents thereof to the residue obtained in step (viii),
(x) filtering the reaction mass obtained in step (ix) and concentrating the filtrate to yield fosaprepitant dibenzyl ester of purity >96% as an oil,
(xi) dissolving the oil obtained in step (x) in at least one solvent or a mixture of solvents thereof,
(xii) adding N-methyl-D-glucamine and Pd/C to the reaction mass obtained in step (xi) and hydrogenating the reaction mass for 8 h to 14 h at 2 kg to 8 kg pressure,
(xiii) filtering the reaction mass obtained in step (xii),
(xiv) adding metal scavenger to the reaction mass obtained in step (xiii) and stirring for 8 h to 14 h, and
(xv) obtaining fosaprepitant dimeglumine of purity >99% from the resulting reaction mass of step (xiv) on further work-up.

2. The process according to claim 1, wherein the solvent used for preparing the fosaprepitant dimeglumine in step (ii), step (v), step (vii), step (ix) and step (xi) of the process is selected from the group consisting of a polar solvent and a non-polar solvent or a mixture thereof.

3. The process according to claim 1, wherein inorganic acid used in step (iii) is boric acid.

4. The process according to claim 1, wherein metal scavenger used in step (xiv) is selected from triphenyl phosphine or tributyl phosphine.

* * * * *